United States Patent [19]

Verdiere et al.

[11] Patent Number: 4,791,481
[45] Date of Patent: Dec. 13, 1988

[54] METHOD FOR LOCATING WEFT THREAD DEFECTS IN FABRIC

[75] Inventors: Piet Verdiere, Kortrijk; Michel Vandeweghe, Wijtschate-Heuvelland, both of Belgium

[73] Assignee: Picanol N.V., Belgium

[21] Appl. No.: 63,316

[22] Filed: Jun. 18, 1987

[30] Foreign Application Priority Data

Jul. 11, 1986 [NL] Netherlands .......................... 8601818

[51] Int. Cl.$^4$ .............................................. H04N 7/00
[52] U.S. Cl. .................................... 358/101; 358/107; 26/70; 356/238; 356/431; 139/291 R; 139/1 R
[58] Field of Search ............... 139/1 R, 291 R; 26/70; 356/238, 431, 430; 358/93, 101, 107

[56] References Cited

U.S. PATENT DOCUMENTS

| | | | |
|---|---|---|---|
| 2,935,559 | 5/1960 | Dornier | 358/106 |
| 2,984,699 | 5/1961 | Dornier | 26/70 |
| 4,582,095 | 4/1986 | Kronholm | . |
| 4,583,181 | 4/1986 | Gerber et al. | 358/106 |

FOREIGN PATENT DOCUMENTS

| | | |
|---|---|---|
| 859668 | of 1978 | Belgium . |
| 3435391 | 4/1985 | Fed. Rep. of Germany . |
| 2041693 | 9/1980 | United Kingdom . |

Primary Examiner—Henry S. Jaudon
Attorney, Agent, or Firm—Bacon & Thomas

[57] ABSTRACT

A process for locating weft thread defects in woven fabrics includes using a macro (close-up) lens and video camera to produce an enlarged image of the fabric, and then observing and evaluating the weft pattern from the video generated image. Transmissive and reflecting illumination may be used on the fabric to enhance the video image. Evaluation and measurement of weft thread positions is carried out by direct visual observation or by using computerized pattern recognition systems with micro processor techniques involving digitizing the video image. A relaxation defect of weft thread is determined by measuring variation between weft thread spacing when the fabric is viewed from two different viewing angles.

4 Claims, 2 Drawing Sheets

METHOD FOR LOCATING WEFT THREAD DEFECTS IN FABRIC

BACKGROUND OF THE INVENTION

The present invention concerns a method for locating weft thread defects in a fabric. This method can be put into practice, for example, in a weaving loom immediately after the weaving of the fabric or at a special check point independently of the weaving loom.

More particularly, the invention concerns a method for quantifying a value corresponding to the fabric quality and more particularly the relative location of the weft threads.

It is known that defects can occur in fabrics as a consequence of improper positioning of the weft threads during weaving. Generally speaking, these defects are related to the starting strips which are formed due to the fabric being more open or tight at various locations than what is normal. Relaxation starting strips can also occur if one or several weft threads are located at a position that is too deep if, for example, one weft thread is inserted into the fabric with excessive tension.

It is known that, in order to track down such defects at the weaving loom and more specifically, to locate variations of fabric density resulting from such defects, methods can be used that enable rapid adjustment of the weaving process. According to U.S. Pat. No. 4,582,095 such a check is carried out at the weaving loom by using a close up lens and a video camera to generate an image of the fabric, following which the image is digitized by the use of a matrix (i.e., a computer pattern recogntion system) and the distance between weft threads is calculated from this information.

This known method has, however, the disadvantage that fabrics without a contrasting profile cannot be checked simply by using this technique. Indeed, in the case of fabrics with a large fabric density and also in the case of fibrous fabrics, the edges of the weft threads are difficult to distinguish and it is consequently quite impossible to carry out an automatic check in a relatively simple way.

SUMMARY OF THE INVENTION

In order to overcome this disadvantage, the present invention contemplates a method for checking the location of weft thread defects in a fabric, whereby the aforesaid disadvantage is systematically avoided. This method comprises mainly the generation of a close-up image of the fabric by means of a video camera, and then using the image to carry out a check for deviations between weft thread locations, including the step of enhancing image quality by using contrast enhancing illumination. According to a first embodiment, this contrast enhancing illumination mainly comprises the illumination of the fabric from an angular direction projected from the same side of the fabric as the location of the video camera (reflective lighting). According to an alternative embodiment, the contrast enhancing illumination is achieved by illuminating the fabric from behind (transmissive lighting).

The evaluation of the image obtained by means of the video camera can be carried out by direct observation or automatically. In a first example, this result is obtained by using a scaler instrument, while in the second case a computerized pattern recognition system (CPR) is used.

According to another embodiment, the present invention contemplates determining weft depth optically and matematically, whereby the deviation between the positions of the weft threads can be measured and calculated from observable relaxation defects in the fabrics.

DESCRIPTION OF THE DRAWINGS

In order that the characteristics of the invention may be better understood, the preferred embodiment is illustrated in the drawings, wherein.

DETAILED DESCRIPTION OF PREFERRED EMBODIMENTS

Figures 1, 2:
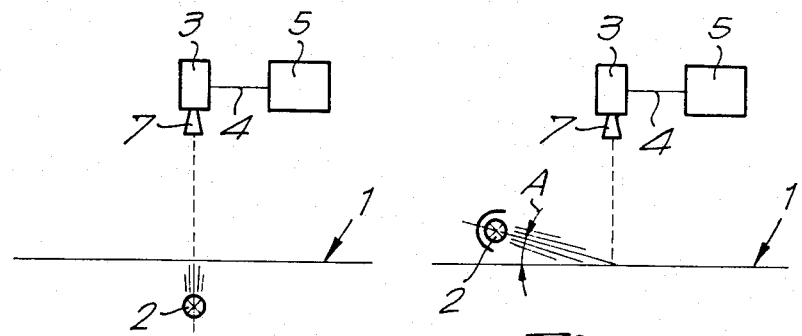
FIG. 1 illustrates the overall system contemplated by the invention wherein the contrast enhancing illumination is provided by illumination directed through the fabric.
FIG. 2 illustrates the overall system contemplated by the invention wherein the contrast enhancing illumination is provided by reflected light directed at an angle to the front of the fabric.

With reference to FIG. 1, the method in accordance with the invention is carried out by illuminating fabric 1 to be evaluated from behind, for instance by placing a light source 2 under the fabric, while a video camera 3 is directed to the opposite (front) side of the fabric. The signals 4 from the video camera are then evaluated by direct observation or automatically in processing unit 5.

Figure 3:
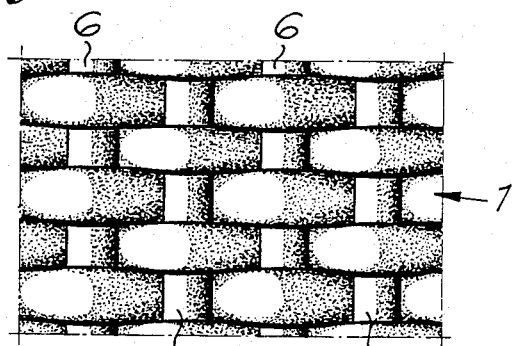
FIG. 3 shows the image of the fabric as seen by the video camera in the case of reflective illumination.

If the fabric is very tightly woven, preference will be given to the embodiment illustrated in FIG. 2 (reflectance illumination). In this case, the light source 2 is located on the front side of the fabric 1 in such a way that it is illuminated by inclined lighting projected at a predetermined angle towards the fabric. The advantage is thus obtained that the weft threads 6 are illuminated along one side, while on the other side a shadow effect is achieved. Quite obviously, this method produces a sharp and highly contrasted image as illustrated in FIG. 3.

Figure 4:
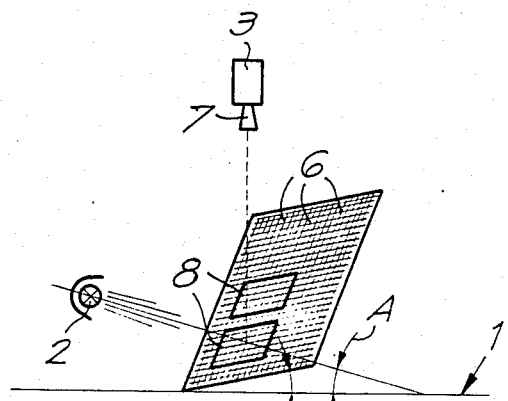
FIG. 4 shows a schematic illustration of another method according to the invention for checking a complete fabric.

In the case of manual evaluation of the image in processor 5, the unit 5 will be mainly composed of a scaling instrument. This is a device that superimposes two vertical lines and one horizontal reference line onto the image generated by video camera 3. These three lines can be moved (i.e., scanned) manually over the image by rotating potentiometers. In accordance with this method the two vertical lines are placed on two successive bright-dark contrast transitions and the distance between the two vertical lines is recorded. Similar distances can then be recorded at several locations on the fabric in order to determine the average of any deviations between weft thread positions. In the case of non-linear contrast transitions, the lines of the scalers are usually shifted according to the average transition location.

Where automatic checking of the relative locations of the weft threads 6 is to be made, a processing unit 5 equipped with a computerized pattern recognition system (CPR) such as, for example, a system described in U.S. Pat. No. 4,582,095. By means of a CPR system, optical images of the light and dark points of the fabric 1 that have been observed by means of a macro lens 7 can be digitized and afterwards read and interpreted to provide the desired information. The fabric 1 preferably is evaluated in a systematic way. As illustrated in FIG. 4, several images can be taken at points located near each other and evaluated. This way, it is possible to then compare these images with measurements taken from a perfect or "reference" fabric. As a result of observations made at different locations 8 near each other that all involve the same weft threads 6, it is possible to calculate an average from these results in order to obtain a quantitative evaluation of the fabric quality in respect to the position of the weft threads.

Figure 5:
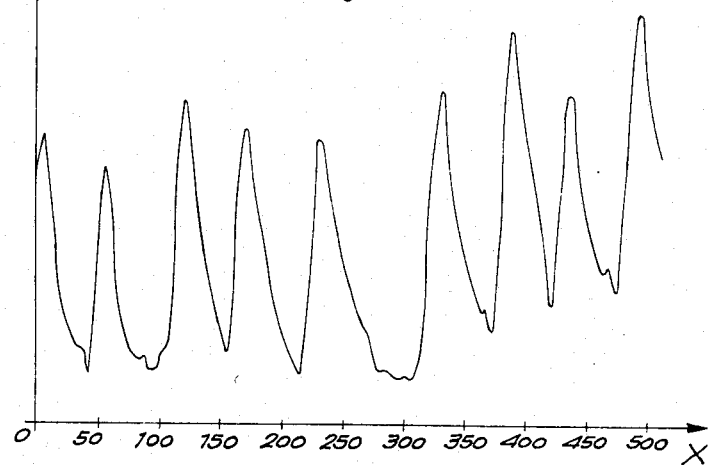
FIG. 5 illustrates a graphical curve depiction of weft spacing using a computerized pattern recognition system; and, FIGS. 6 and 7 illustrate a method for measuring thread depth according to the invention.

The aforesaid CPR system can for instance, use a bar pattern of 512×512 points (pixels, or picture elements) corresponding to about 5 weft threads per image, which corresponds to a resolution of about 1% for each weft thread. in order to obtain very quickly reliable results, use shall be made of the following algorithm in accordance with this invention. The bar pattern is first of all oriented in such a way that the pattern columns are parallel to the direction to the weft threads. Then, 512 values of light intensity are counted, column after column. In this way we get a series of 512 values indicating the total light intensity of each vertical line or weft. These values have a typical pattern as illustrated in FIG. 5, wherein the distances between the successive maximum slopes correspond to the distance between the wefts. The distance between the wefts can be automatically determined from the aforesaid values by using a micro-processor in accordance with conventional procedures. The micro-processor then computes a numeric value of the distances using a suitable algorithm.

In the case of noisy images, for instance when the fabric is extremely intricate, the determination of the aforesaid maximum slopes may be somewhat difficult because the maxima of the curves may not be clearly delineated. This problem can be avoided by replacing each value on each point of the bar pattern by the average of (i) the value itself, and (ii) the value of the adjacent points, whereby, according to the present invention, only the adjacent points located on the same vertical line (weft) are taken into account to generate the slopes. This counting following vertical lines followed by the determined value has an advantage by comparison with the usual suppressing filter, i.e., where each point is replaced by the average of its 8 adjacent points, because it runs 10 times faster.

In the case of a fabric with highly reflective warp threads, the image of the fabric is subdivided into strips having the width of one warp thread. The odd strips are analyzed first, for instance and then the even stripes are evaluated.

Figure 6:
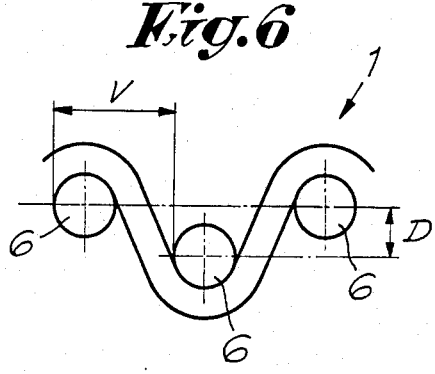
Figure 7:
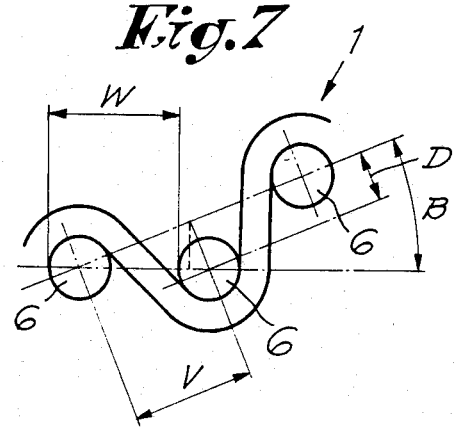

According to another embodiment of the invention, weft defect analysis based on the depth of wefts is possible. This method is based on the fact that (with reference to FIGS. 6 and 7) the depth D of defective weft threads is different than their normal depth due to a relaxation defect. In this case, the depth D is determined by several successive distance measurements. As illustrated in FIG. 6, the horizontal distance V is dettermined by any suitable visual or CPR system. Thereafter, the fabric 1 is rotated at an angle B about an axis extending parallel to the weft threads and with respect to the observation direction of the video camera 3 (see FIG. 2). The distance between wefts W is then determined between two successive weft threads 6 in the rotated position. The value D can then be calculated from the mathematical equation:

$$W = V \cdot \cos B + D \sin B$$

An angle of between 30 and 50 degress is preferably chosen for B because this value of B generally give a very contrasting image. The depth D will preferably be calculated by taking the average results of several measurements which have been carried out with different angles.

The present invention is by no means limited to the embodiments described by way of examples and illustrated in the figures of the drawings, but this method for checking the location of the weft threads of a fabric can be put into practice according to different alternative solutions without departing from the scope of the present invention.

We claim:

1. A method for locating the depth of weft threads in a woven fabric including the steps of:
    (a) illuminating the fabric surface with contrast enhancing light;
    (b) generating a close-up first video image of the illuminated fabric surface located in a first plane relative to the video viewing angle, the image depicting the surface profile of the woven threads, in particular the weft thread;
    (c) from the video image, determining the distance V between adjacent weft threads;
    (d) rotating the plane of the fabric relative to the video viewing angle about an axis extending parallel to the weft threads and generating a close-up second video image of the illuminated fabric surface in a second plane;
    (e) from the second video image determining the distance W between the adjacent weft threads;
    (f) determining the weft thread depth D according to the formula $$W = V \cdot \cos B + D \sin B.$$

2. The method as claimed in claim 1 wherein the steps of determining the distances between wefts is carried out by direct visual observation of the video image using a scaling instrument.

3. The method as claimed in claim 1 wherein the steps of determining the distances between wefts is carried using computerized pattern recognition techniques including generating columns of image pixels corresponding to the video image and arranged parallel to the directions of the weft threads, measuring the light intensity of all points in each column, column-by-column; generating a graphical curve depicting the light intensities measured; determining the distances between wefts by measuring the distances between the maximum intensity slopes of the light intensity curve.

4. The method as claimed in claim 1 wherein the fabric is highly reflective, including
    subdividing the image of the surface into stripes, each stripe having a width of a single warp thread;
    determining the distances V and W using a 2-stage process of fisrt obtaining the measurements used for such determination by first using alternate stripes, followed by using the other alternate interleaved stripes.

* * * * *